(12) United States Patent
Diaz

(10) Patent No.: US 6,682,939 B2
(45) Date of Patent: Jan. 27, 2004

(54) CHEMICAL SAMPLER SYSTEM AND CONTAINER

(75) Inventor: Ramon Alberto Diaz, Port Arthur, TX (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 10/037,533

(22) Filed: Jan. 4, 2002

(65) Prior Publication Data

US 2002/0078766 A1 Jun. 27, 2002

Related U.S. Application Data

(63) Continuation of application No. PCT/US99/19562, filed on Aug. 25, 1999.

(51) Int. Cl.[7] .................................................. G01N 1/20
(52) U.S. Cl. ................. 436/174; 73/863.11; 73/863.81; 73/864.51; 73/864.62; 73/864.63; 422/62; 422/102; 436/176; 436/180
(58) Field of Search .................................. 436/174, 176, 436/177, 180; 422/62, 99, 100, 101, 102, 103, 119, 131; 73/863.11, 863.12, 863.81, 863.84, 863.85, 863.86, 864.51, 864.62, 864.63

(56) References Cited

U.S. PATENT DOCUMENTS

| 2,639,840 A | * | 5/1953 | Wons ........................ 222/485 |
| 4,651,574 A | * | 3/1987 | Spencer ................... 73/863.86 |
| 5,604,320 A | * | 2/1997 | Boyd ...................... 73/863.86 |
| 5,705,572 A | * | 1/1998 | Yi et al. ..................... 525/339 |

OTHER PUBLICATIONS

Chemical Abstract No. 102:116203, Johnson et al, Oil & Gas Journal No. 83, vol. 6, pp. 98–100 (1985).*

* cited by examiner

Primary Examiner—Jan Ludlow
(74) Attorney, Agent, or Firm—Nancy T. Krawczyk; David E. Wheeler

(57) ABSTRACT

A method and apparatus for sampling chemicals prevents exposure of laboratory personnel to the chemicals being tested and to volatile solvents or chemicals that may be mixed with the tested chemicals. The apparatus includes a sampling line connected to the source of the chemicals, a cooling means for reducing the temperature of the chemicals, and a sample holder for containing the sampled chemicals. In the method, the chemicals are removed from their source, cooled, and contained in the presence of a shortstop chemical, i.e. a chemical designed to terminate any chemical reaction that may be taking place when the chemicals are sampled. The apparatus also captures and contains any volatile solvents or chemicals that may be mixed with the chemicals being tested.

15 Claims, 9 Drawing Sheets

CHEMICAL SAMPLER SYSTEM AND CONTAINER

This is a Continuation of International Application Serial No. PCT/US99/19562 filed on Aug. 25, 1999, presently pending.

TECHNICAL FIELD

The invention relates to a method and apparatus for the in line sampling of chemicals which undergo a chemical reaction in line.

BACKGROUND ART

When chemical production is carried out on an industrial scale, the chemical reactions leading to a chemical product are often carried out while the chemicals which undergo the reaction are pushed through pipes or lines in the industrial plant, at a temperature conducive to the chemical reaction, in the presence of the necessary catalysts. In order to maximize the yield, and to ensure that the correct product is produced (in complex organic chemical reactions there is often a number of possible products which can be produced given the same starting materials, the products depending on the reaction conditions).

For purposes of illustration, reference is made to the production of polymer cement samples, wherein precursor polymer materials are pushed through a polymerization reactor in a solvent solution, usually a hydrocarbon solvent solution. For the purposes of quality control, it is desirable to check the progress of the chemical reaction at certain points in the line in order to make sure that the proper precursors are being formed at the proper stage of the reaction. This can be done by taking a sample of the reaction mixture, quenching (i.e., stopping the chemical reaction so that the chemical makeup of the materials sampled does not change before an analysis can be made), and analyzing the chemicals present at the point in time that the sample is taken out of the reaction line.

Since such a sample is captured at reaction conditions, the chemicals of interest are usually at elevated temperatures and are surrounded by volatile hydrocarbons and other volatile organic compounds. Chemicals at high temperatures, and exposure to volatile hydrocarbons raise safety issues for the laboratory operator, or any technician that is charged with collecting individual samples.

Prior to the present invention, a procedure used to obtain such samples was to take a sample of the reaction materials, and to dump it into a jar containing a shortstop chemical (i.e. a chemical used to stop the chemical reaction). In some embodiments, the jar used to collect the reaction materials was lined with a chemical resistant plastic, and the shortstop chemical was mixed with the reaction chemicals in the plastic material lining the sample collection jar.

U.S. Pat. No. 4,651,574 teaches a delivery system for testing a sample that includes a cooler. The sampling system described by the patent, however, is not adequate for testing rubber and plastics polymerization processes.

It is an object of the present invention to provide a sampler that reduces or eliminates the laboratory technicians exposure to volatile hydrocarbon, and exposure to the reaction chemicals themselves. Other objects of the invention will be apparent from the following description and claims.

DISCLOSURE OF INVENTION

An apparatus for sampling in-line chemicals comprises (a) a conduit leading from a chemical reaction line to a sample holder, (b) a cooling means associated with the conduit, (c) a sample holder connected to the conduit, the sample holder comprising a container having two opposed ends and removable covers associated with each end, (d) a chemical agent contained within the sample holder, the chemical agent being adapted to interrupt a chemical reaction carried out in the chemical reaction line, and (e) means for mixing the chemical agent with chemicals from the chemical reaction line.

In the illustrated embodiment, the cooling means is a cooling coil and the conduit leading from the chemical reaction is contained within the tubing of the cooling coil.

The apparatus may further include a vacuum for exhausting volatile solvents and chemicals from a sample.

The sample holder may be made from a transparent material, and the apparatus may further include a sample holder receiver adapted to fit over the sample holder and to hold a valve for controlling inflow of a sample into the sample holder. The valve preferably contains an eductor removing volatile solvents and chemicals from around the sample.

In the illustrated embodiment, the mixing means is a chemical resistant liner contained within the sample holder, which is used for containing the shortstop chemical agent and receiving chemicals from the chemical reaction line, whereby the shortstop chemical agent is mixed with the reaction chemicals by kneading the chemical resistant liner.

In the illustrated embodiment, the sample holder is a cylinder having two opposed threaded ends, and threaded covers are associated with each threaded end. One threaded cover is fitted with a septum for receiving a needle for delivering the sample. And the liner is a chemically resistant, flexible plastic material.

In the illustrated embodiment, the means for cooling the sample is a cooling coil comprising tubing associated with the conduit, whereby the conduit is contained within the tubing.

Also provided is a method for sampling in-line chemicals comprising the steps of (a) inserting a valve into a chemical reaction line, (b) drawing a sample from the chemical reaction line while a chemical reaction is in progress, (c) connecting a sample holder to the conduit, the sample holder comprising a container having two opposed ends and removable covers associated with each end, (d) tansporting the sample through cooling means for reducing the temperature of the sample delivered to the holder, and (e) mixing the sample with a shortstop chemical agent adapted to stop the chemical reaction.

The method may include the further step of evacuating volatile solvents and chemicals from around the sample in the sample holder and providing an evacuated box for storing the sample. The sample holder may be provided in the form of a cylinder which is threaded on both ends and having a threaded cover associated with each end. The cylinder may contain a chemical resistant liner, and a shortstop chemical agent contained within the liner.

The method may be carried out by removing the bottom cover from the cylinder, and mixing the sample with the shortstop chemical agent by kneading the liner.

DETAILED DESCRIPTION OF THE INVENTION

Figure 1:
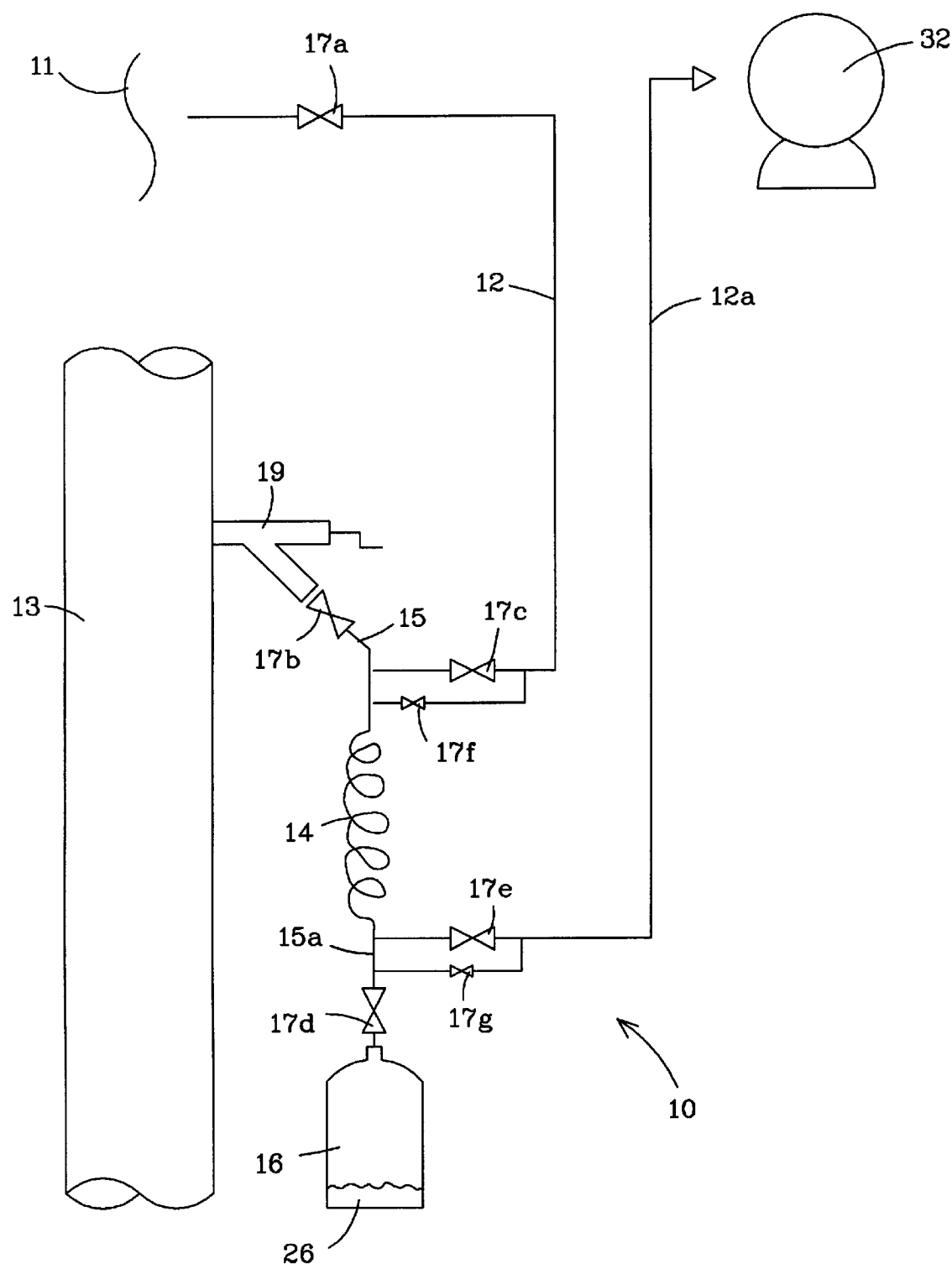
FIG. 1 illustrates a schematic view of the sampling system of the invention.
Figure 2:
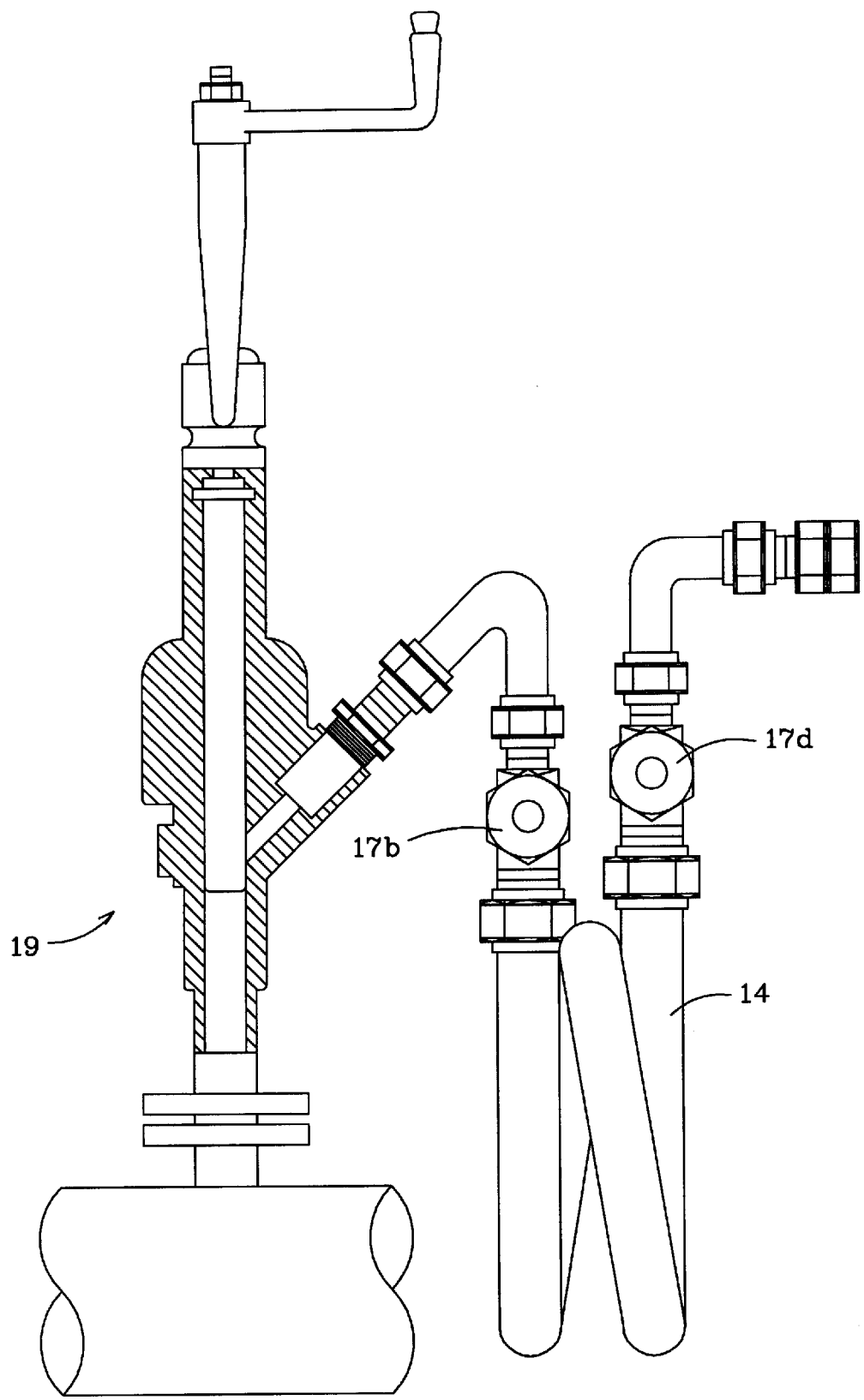
FIGS. 2 and 2a illustrates valves and cooling coils of the sampling system.
Figure 2A:
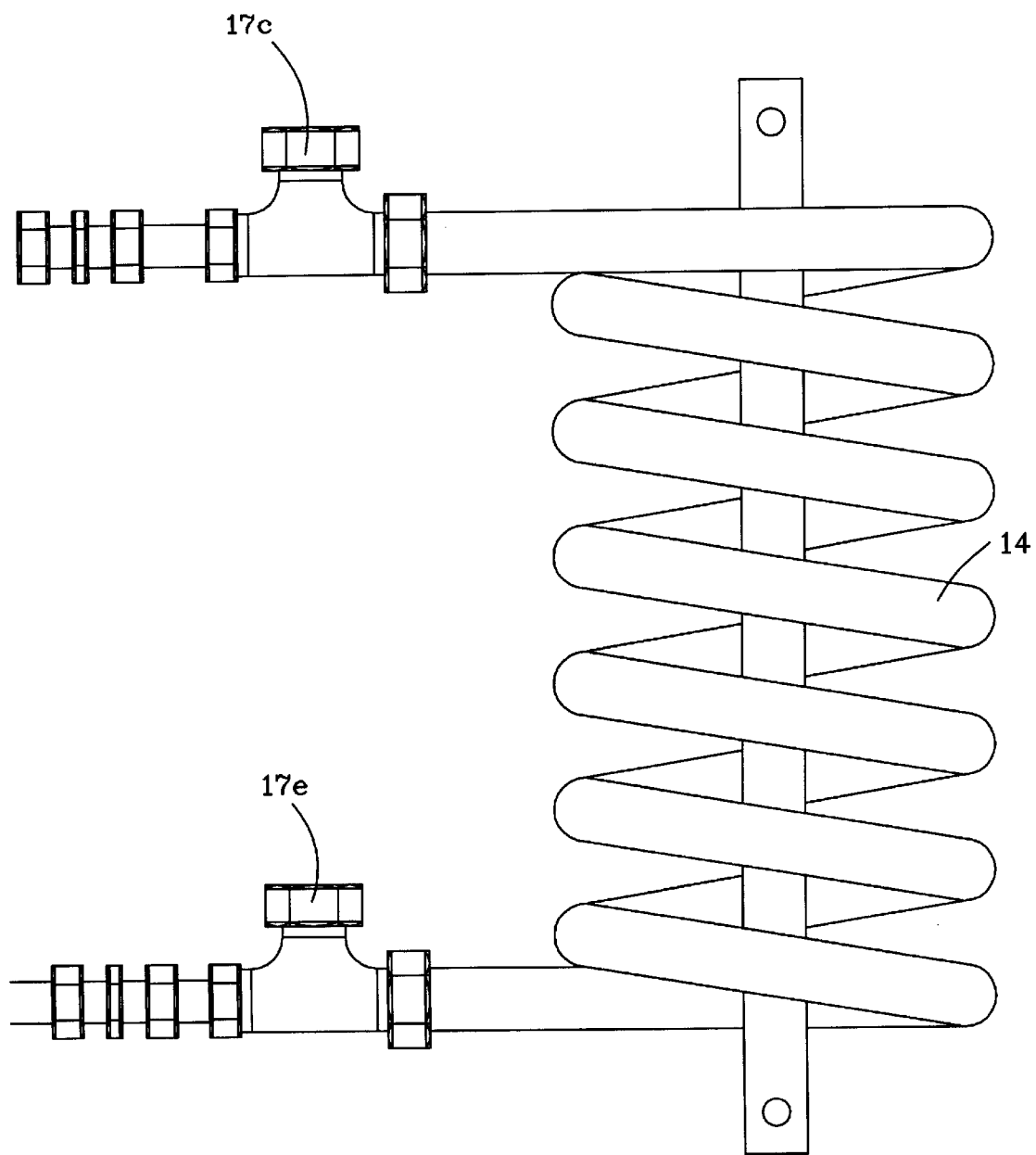

With reference now to FIG. 1, in an illustrated embodiment, the sampling system of the invention is shown schematically. In the illustrated embodiment, the apparatus 10 comprises a valve 19 (in the illustrated embodiment a Strahman valve, FIG. 2 and FIG. 2a) which is attached to the reaction line 13 at the point where chemical analysis is desired. For purposes of illustration, the invention will be described with reference to a polymer cement sample which is reacted in the presence of an n-hexane solvent. Those skilled in the art will recognize that the apparatus and method of the invention can be used with other types of chemical reactions.

The polymer cement sample in reaction line 13 has a reaction temperature of about 180° to 210° Fahrenheit, and it is desirable to reduce the temperature of the reaction mixture, both for the safety of the operator by reducing the vapor pressure around the sample, and to help stop polymerization within the sample. Stopping polymerization assures that the status of the chemical reaction mixture, at the time the sample is collected, reflects accurately the chemicals present in the reaction mixture at a specific place and time in the reactor.

Accordingly, valve 17b is opened to draw off some of the chemical reaction mixture, which then passes through line 15 into cooling coil 14. When the reaction mixture is cooled in cooling coil 14, it then passes into line 15a and through valve 17d into the sample holder 16. A shortstop chemical 26 contained within sample holder 16 is used to neutralize the catalyst, or to neutralize the reactive chemicals in the reaction mixture, to further prevent any chemical change to the reaction mixture.

A polymerization reaction, such as that used for forming polymer cements, which takes place in the presence of a solvent, such as n-hexane or cyclohexane, or other solvents used in the industry, is known as solution polymerization.

Since n-hexane is readily available for use in the reaction, it has been found convenient, in the illustrated embodiment, to also use n-hexane as the coolant for cooling coil 14. Those skilled in the art will recognize that other coolants, including water, can be used in the cooling coil.

When a sample is being captured, n-hexane from solvent source 11 is released through valve 17a into line 12, and through valve 17c into cooling coil 14. In the illustrated embodiment, the sample line 15 is a conduit which passes through, i.e. inside, the tubing comprising cooling coil 14. After the n-hexane passes through the cooling coil 14, it is released through valve 17e into line 12a, where it can be captured and reused in the reaction process, or used for cooling another sample. A vacuum apparatus 32 can induce the flow of n-hexane into line 12a.

In the illustrated embodiment, valves 17f and 17g are used as reflux valves for recycling hexane from the sample back into the hexane flow used as the coolant. If a different coolant is used, the effluent from the sample can be directed to a separate receiver. Accordingly, the apparatus cools the sample and removes volatile solvents from the sample before the sample is introduced into the sample holder 16.

Figure 3:
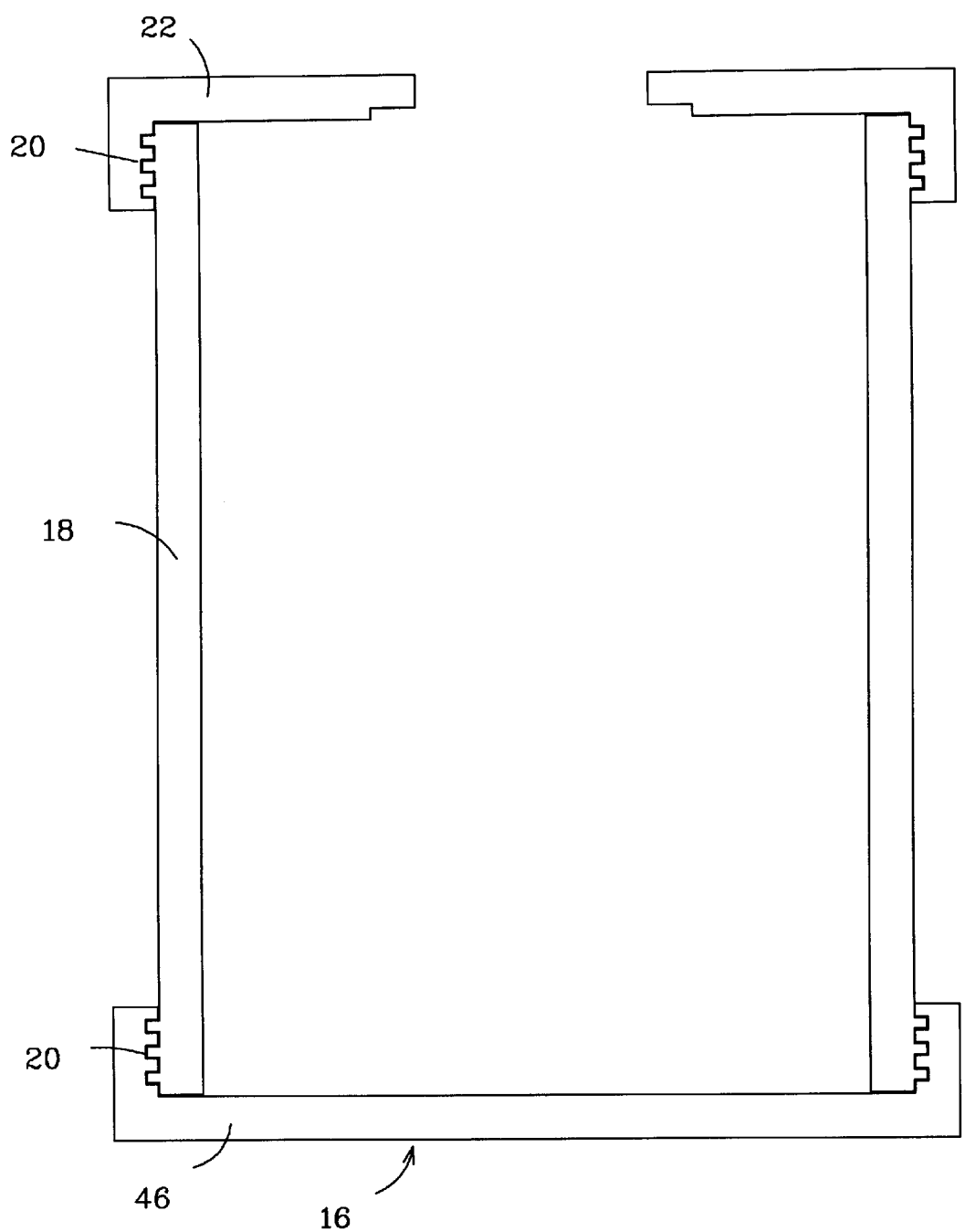
FIG. 3 illustrates a sample holder of the invention.

With reference now to FIG. 3, in the illustrated embodiment, sample holder 16 comprises a cylinder 18 which has threads 20 at each end thereof. A threaded top cover 22 is attached to one end of cylinder 18, and bottom cover 46 is attached to the opposite end thereof.

Those skilled in the art will recognize that the sample holder may take other forms, it being important for the method specifically described herein only that the sample holder be accessible from opposed ends thereof, so that one end can be used for receiving a sample, and the opposite end can be used for gaining access to the cooled and quenched sample.

In the illustrated embodiment, the sample holder 16 is made from a transparent material. Preferred materials are polycarbonate and Plexiglas since such materials are chemically resistant and break resistant. Other transparent materials may be used.

A transparent sample holder 16 is desired so that the sample and shortstop chemical can be observed while a sample is being collected. As the apparatus becomes automated with some of the features described herein, and as modified by those skilled in the art, the transparency of sample holder 16 becomes less important.

Figure 4:
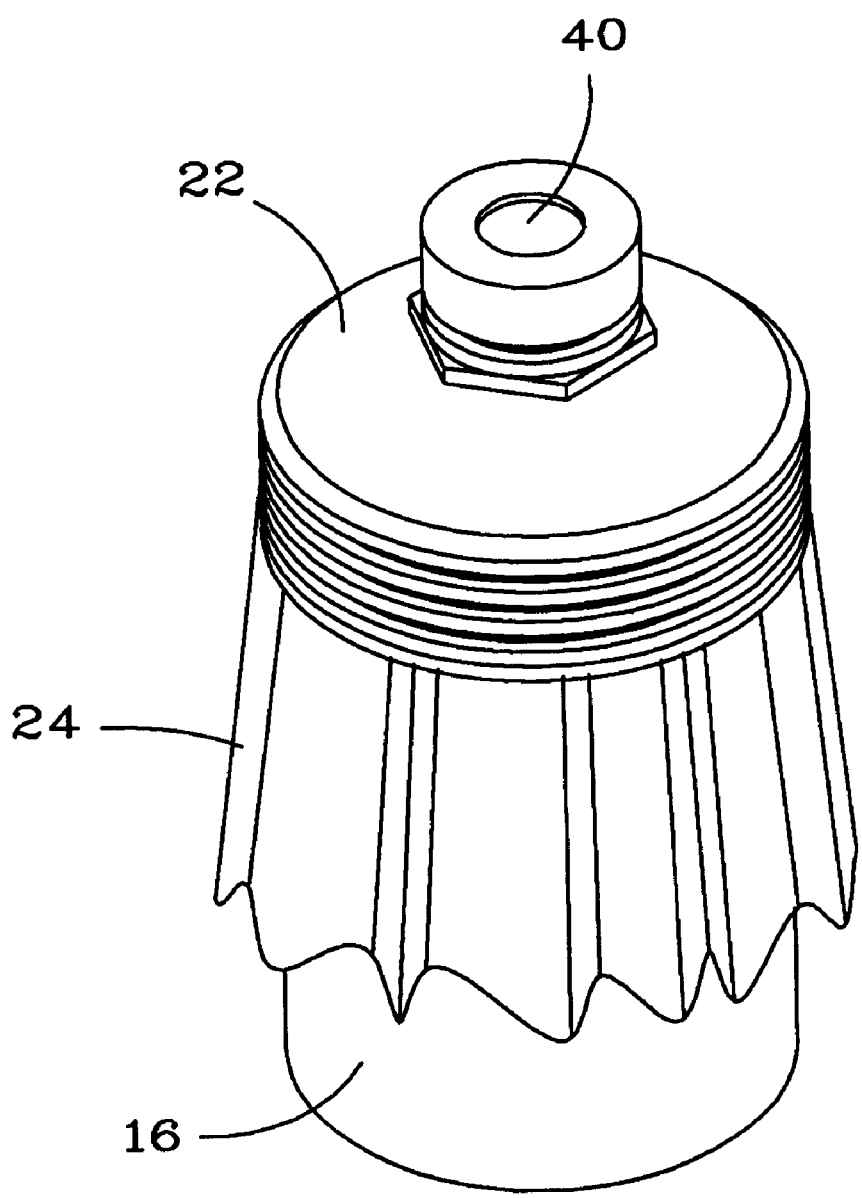
FIGS. 4 and 4a illustrate a top cover of the sample holder of the invention.
Figure 4A:
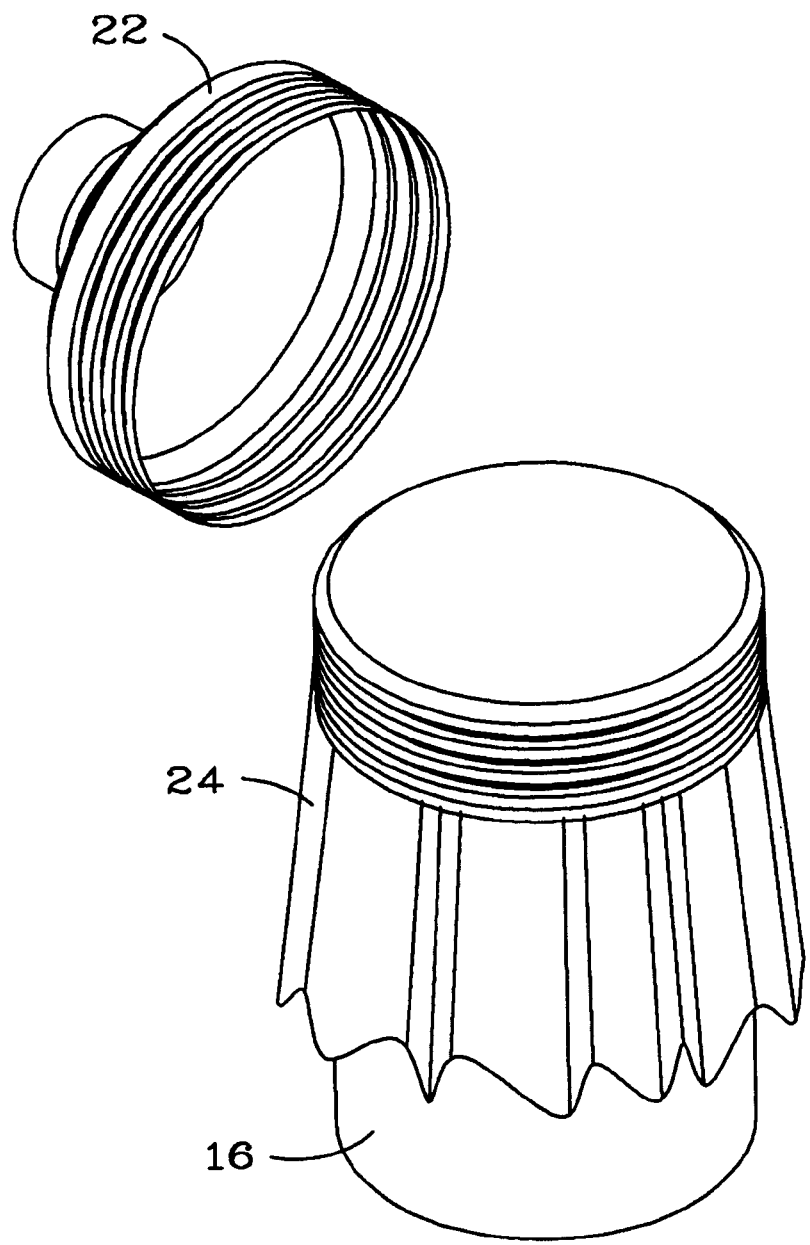

With reference to FIGS. 4 and 4a, top cover 22 of the sample holder 16 has attached thereto a septum 40, whereby a sample can be introduced into sample holder 16 using a needle inserted through septum 40.

Septum 40 is preferably made of a rubbery material which is distorted when penetrated by needles, and returns to shape when the needle is removed, thereby closing the hole made by the needle penetration. Examples of such rubbery materials are well known to those skilled in the art.

As illustrated, sample holder 16 is lined with a chemically resistant plastic material 24, and when a sample has been introduced into the sample holder 16, the bottom cover 46 thereof can be removed, and the shortstop material 26 (also contained within chemically resistant plastic material 24) can be kneaded through the chemically resistant plastic 24 into the sample material, to interrupt the chemical reaction of the sample.

Those skilled in the art will recognize that other means can be used for mixing the sample and the shortstop material, such as a magnetic stirrer. When using other mixing devices, it may be preferred to use disposable sample holders instead of the plastic liner material 24. The choice of the type of sample holder, and the way that it is used in the method of the invention, is a matter of choice for one skilled in the art.

Figure 5:
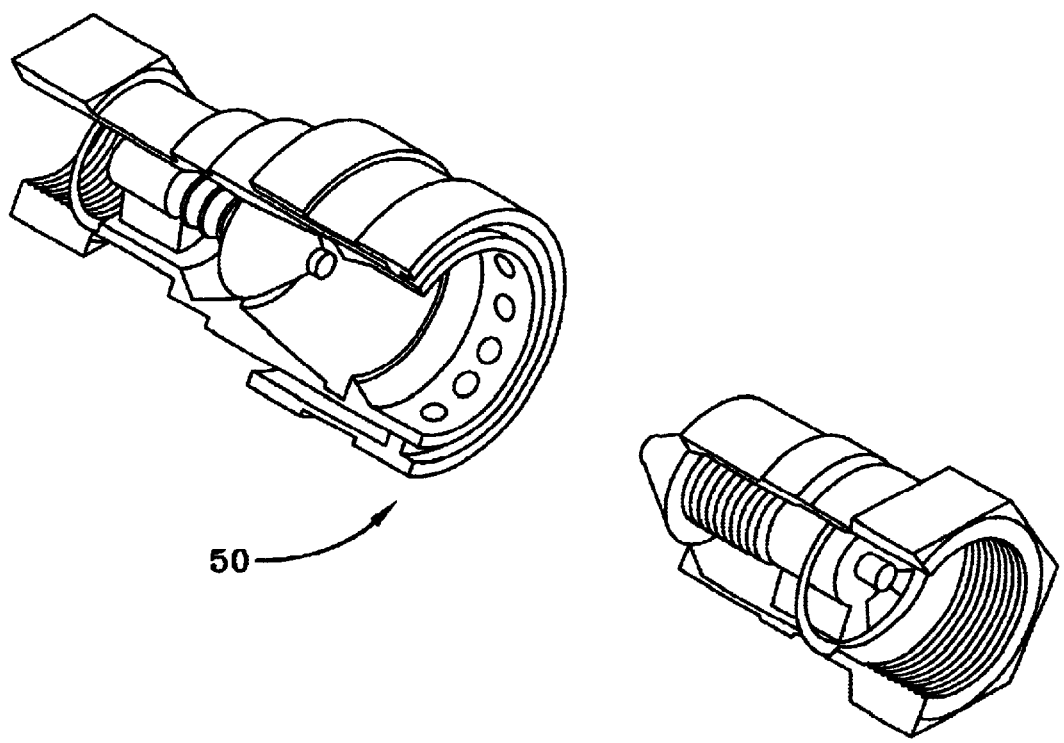
FIG. 5 illustrates a prior art valve used with the sample holder.

With reference now to FIG. 5, a prior art valve, e.g., from Texas Sampling, Inc., which contains one delivery line inside another is illustrated. Such a valve 50 is used in conjunction with a needle 44, which is used to deliver sample through septum 40 in the top cover 22 of sample holder 16. The valve is also equipped with an eductor 42, which is used to evacuate solvents from the sample holder 16 where they are recycled through line 12a. As illustrated, sample from line 15 and coolant from line 12 pass through entry portion 52 of the valve, and sample passes through needle 44 into sample holder 16, and coolant and solvent from the sample passes through the eluter 54 into line 12a.

Figure 6:
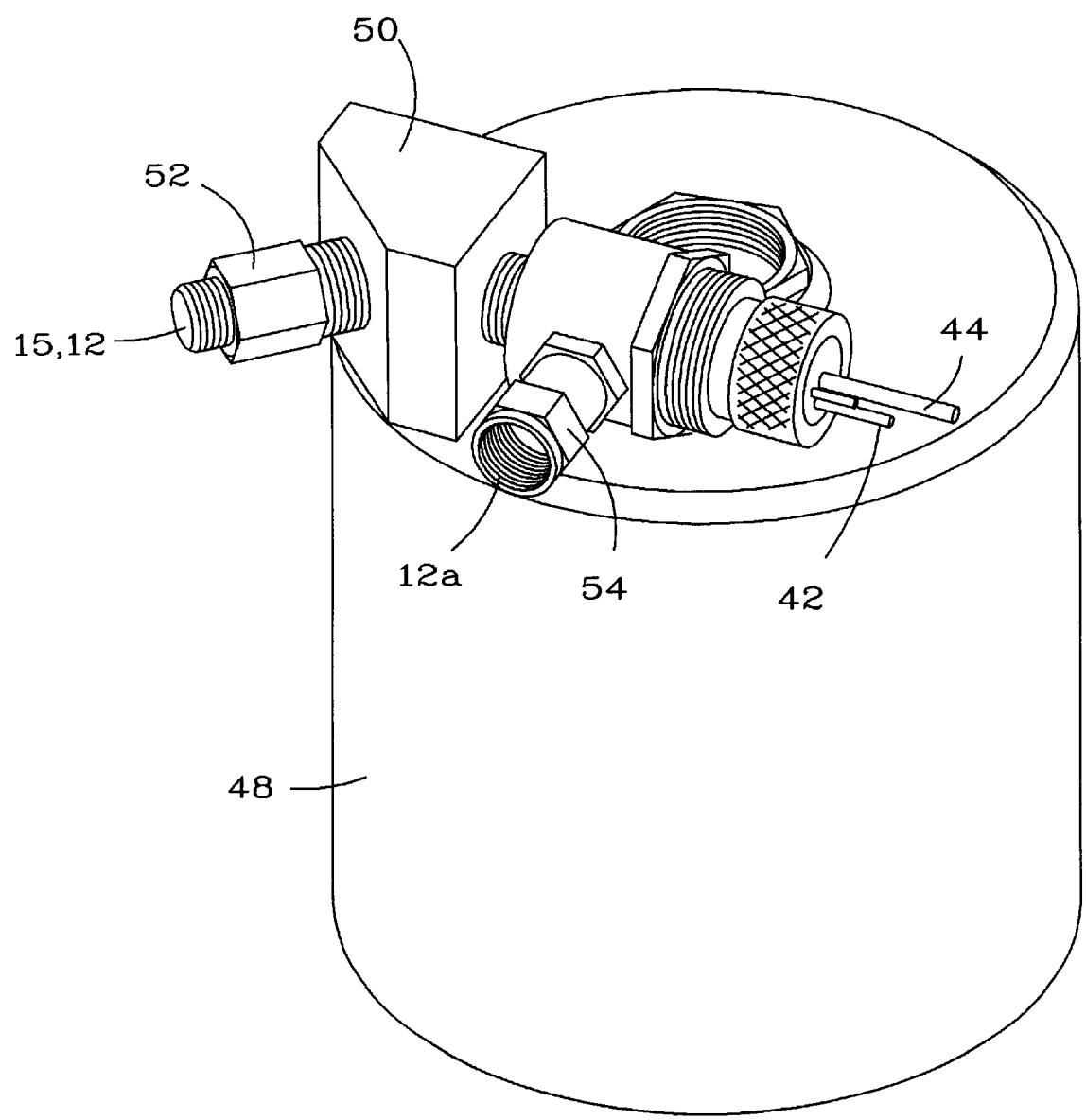
FIGS. 6 and 6a illustrate a sample holder receiver used with the apparatus of the invention.
Figure 6A:
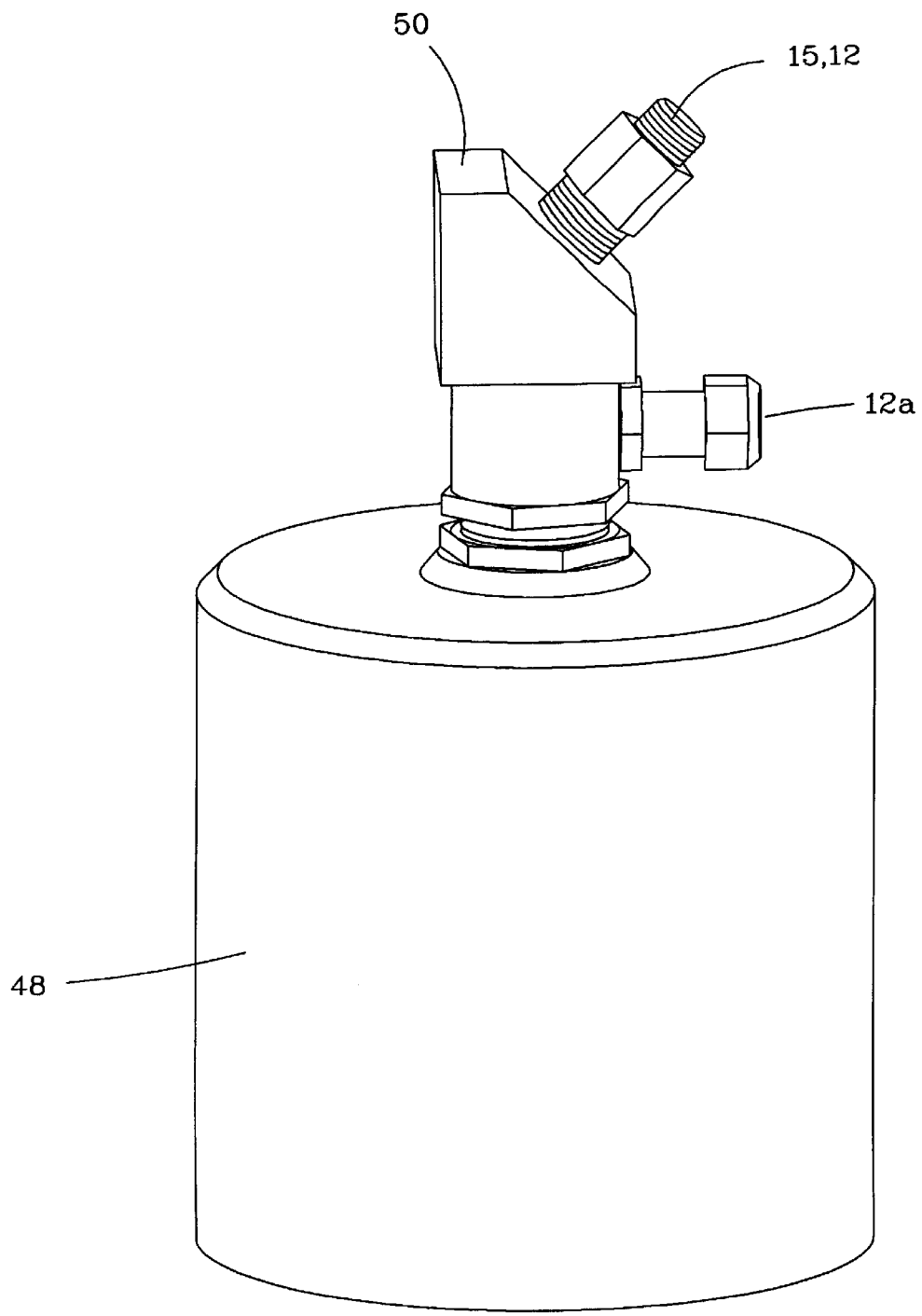

With reference to FIGS. 6 and 6a, to stabilize the sampling procedure, valve 50 is preferably attached to a substantial (e.g. a stainless steel container) box or chamber which is used as a sample holder receiver 48. Containment of sample holder 16 in such a receiver 48 may further reduce exposure of the laboratory technician to the volatile solvents.

Receiver 48 provides further separation between the sample and the laboratory technician and provides additional containment in case of an accident involving the sample.

Those skilled in the art will recognize that the valves used to gather sample may be equipped with flow meters which automatically measure the amount of sample obtained, and automatically shut off when the proper amount of sample is obtained, or when some irregularity in the sampling procedure occurs.

The chemical resistant liner 24 may be made of any plastic material which is suitably resistant to the particular chemicals being tested, and is strong enough and flexible enough for its intended use. Such liners may be made of, for example, polyalkylenes, polyamides, polyesters, and halogenated derivatives thereof.

In his use of the illustrated apparatus, the laboratory technician will screw off the top lid 22 of sample holder 16 to insert a plastic liner 24 containing 5 mls of shortstop into sample holder 16. The technician will then screw the top cover 22 back on to sample holder 16, open the valves needed to collect a sample through needle 44, through septum 40, and into the plastic bag 24. Once the sample has been collected, and all the valves closed, a technician will then screw off bottom cover 46 to knead the shortstop into the sample to terminate the chemical reaction of the sample.

The sample can then be stored and analyzed as is convenient for the technician using any desired analytical equipment and tests.

While the invention has been specifically illustrated and described, those skilled in the art will recognize that the invention can be variously modified without departing from the spirit of the invention. The scope of the invention is limited only by the following claims.

what is claimed is:

1. an apparatus for sampling in-line chemicals comprising
   (a) a conduit leading from a chemical reaction line to a sample holder,
   (b) a cooling means associated with said conduit,
   (c) a sample holder connected to said conduit, the sample holder comprising a container having two opposed ends and removable covers associated with each end, one of said covers being fitted with a septum for receiving a needle,
   (d) a chemical agent contained within said sample holder, said chemical agent being adapted to interrupt a chemical reaction carried out in said chemical reaction line, and
   (e) means for mixing said chemical agent with chemicals from said chemical reaction line.

2. The apparatus of claim 1 wherein the cooling means is a cooling coil and said conduit leading from said chemical reaction is contained within tubing of said cooling coil.

3. The apparatus of claim 1 further comprising a vacuum for exhausting volatile solvents and chemicals from a sample.

4. The apparatus of claim 1 wherein said sample holder is made from a transparent material.

5. The apparatus of claim 1 further comprising a sample holder receiver adapted to fit over said sample holder and to hold a valve for controlling inflow of a sample into said sample holder.

6. The apparatus of claim 5 wherein said valve contains an eductor for removing volatile solvents and chemicals from around said sample.

7. The apparatus of claim 1 wherein said mixing means is a chemical resistant liner contained within the sample holder for containing said chemical agent and receiving chemicals from said chemical reaction line, whereby said chemical agent is mixed with said chemicals by kneading said chemical resistant liner.

8. The apparatus of claim 1 wherein said sample holder is a cylinder having two opposed threaded ends, and threaded covers associated with each threaded end.

9. The apparatus of claim 7 wherein said liner is a chemically resistant, flexible plastic material.

10. The apparatus for sampling in-line chemicals of claim 1 wherein the means for cooling said sample is a cooling coil comprising tubing associated with said conduit, whereby said conduit is contained within said tubing.

11. A method for sampling in-line chemicals comprising the steps of
    (a) inserting a valve in a chemical reaction line, creating a conduit,
    (b) drawing a sample from said chemical reaction line while a chemical reaction is in progress,
    (c) connecting a sample holder to said conduit, the sample holder comprising a container having two opposed ends and removable covers associated with each end, one of said covers being fitted with a septum for receiving a needle,
    (d) transporting said sample through cooling means for reducing the temperature of said sample transported to said sample holder, and
    (e) mixing said sample with a chemical agent.

12. The method of claim 11 comprising the further step of evacuating volatile solvents and chemicals from around said sample in said sample holder.

13. The method of claim 11 comprising the further step of providing an evacuated box for storing said sample.

14. The method of claim 11 further comprising providing said sample holder in the form of a cylinder threaded on both ends and having a threaded cover associated with each end, said cylinder containing a chemical resistant liner, and said chemical agent contained within said liner, said chemical agent being adapted to interrupt a chemical reaction in said chemical reaction line.

15. The method of claim 14 comprising the further step of removing said bottom cover from said cylinder, wherein said mixing of said sample with said chemical agent is accomplished by kneading said liner.

* * * * *